United States Patent
Verkerke et al.

(10) Patent No.: US 6,398,714 B1
(45) Date of Patent: Jun. 4, 2002

(54) CARDIAC ASSIST CATHETER PUMP AND CATHETER AND FITTING FOR USE THEREIN

(75) Inventors: G. J. Verkerke, Haren; A. van der Plaats; G. Rakhorst, both of Groningen, all of (NL)

(73) Assignee: Intra-Vasc.NL B.V., Groningen (NL)

(*) Notice: Subject to any disclaimer, the term of this patent is extended or adjusted under 35 U.S.C. 154(b) by 0 days.

(21) Appl. No.: 09/363,711

(22) Filed: Jul. 29, 1999

(51) Int. Cl.[7] .................................................. A61M 1/12
(52) U.S. Cl. ......................................................... 600/16
(58) Field of Search .............................. 600/16, 17, 18

(56) References Cited

U.S. PATENT DOCUMENTS

| | | |
|---|---|---|
| 3,995,617 A | 12/1976 | Watkins et al. |
| 4,014,317 A | 3/1977 | Bruno |
| 6,007,479 A * | 12/1999 | Rottenberg et al. |

FOREIGN PATENT DOCUMENTS

| | | |
|---|---|---|
| FR | 2 144 806 | 2/1973 |
| GB | 1370546 | 10/1974 |
| GB | 1528072 | 10/1978 |
| WO | WO 89/10763 | 11/1989 |
| WO | WO 97/02850 | 1/1997 |
| WO | Wo 98/57698 | 12/1998 |
| WO | WO 99/26676 | 6/1999 |

* cited by examiner

Primary Examiner—Scott M. Getzow
(74) Attorney, Agent, or Firm—Pearne & Gordon LLP (57) ABSTRACT

A cardiac assist catheter pump includes a displacement structure and a catheter. The catheter has an inlet in its distal end portion and an outlet spaced from the distal end portion. The displacement structure alternatingly applies suction for displacing fluid from the catheter to the displacement structure and pressure for displacing fluid from the displacement structure to the catheter. A valve body of the catheter is movable between an inlet position obstructing flow through the outlet and allowing flow through the inlet and an outlet position obstructing flow through the inlet and allowing flow through the outlet. Thus, a simplified construction and a reduced risk of blood clotting is achieved. A catheter and a fitting for such a catheter pump are also described.

24 Claims, 2 Drawing Sheets

CARDIAC ASSIST CATHETER PUMP AND CATHETER AND FITTING FOR USE THEREIN

TECHNICAL FIELD

The invention relates to a cardiac assist catheter pump, to components therefor and to a method for assisting the action of an ailing heart.

BACKGROUND ART

From U.S. Pat. No. 3,995,617 a heart assist catheter pump is known which includes a catheter having a distal end for insertion from the aorta past the aortic valve into the left ventricle. The distal end has inlet openings and a check valve for allowing inward flow. Spaced from the distal end, the catheter has outlet openings and a set of second check valves for allowing outward flow. A pump device communicating with the proximal end of the catheter alternatingly generates a suction causing blood to be withdrawn from the left ventricle into the catheter and to the pump device and an excess pressure causing blood to be reintroduced via the set of second check valves into the heart on the downstream side of the aortic valve.

The second check valves are each formed by an elastic booth at the outside of the catheter. A disadvantage of such a catheter is its use entails a risk of thrombosis. Moreover, such a catheter is of a complicated construction and costly, because valves have to be mounted in the catheter and, at another position in longitudinal direction, to the outside of the catheter.

Another example of such a catheter pump is known from U.S. Pat. No. 4,014,317.

SUMMARY OF THE INVENTION

It is an object of the invention to provide a solution allowing to assist the action of an ailing heart, which overcomes the above-identified problems.

According to the invention, this object is achieved by providing a cardiac assist catheter pump in which the valve arrangement includes a valve body movable between an inlet position obstructing flow through the outlet passage and allowing flow through the inlet passage and an outlet position obstructing flow through the inlet passage and allowing flow through the outlet passage.

The invention further provides a catheter with such a valve arrangement. A further embodiment of the invention is formed by a fitting for a cardiac assist catheter including:
 a tube shaped housing having a coupling for coupling to a distal portion of a catheter on one end and a coupling for coupling to a proximal portion of a catheter on an opposite end; a first passage through the coupling for coupling to a distal portion of a catheter; a second passage through the coupling for coupling to a proximal portion of a catheter; a third passage communicating with the first and second passages; and a valve body movable between an inlet position obstructing flow through the third passage and allowing flow through the first passage and an outlet position obstructing flow through the first passage and allowing flow through the third passage.

Such a catheter and such a fitting are specifically adapted for use as a part of such a catheter pump.

Since the valve arrangement includes a valve body movable between an inlet position at least substantially blocking the outlet passage and clearing the inlet passage and an outlet position at least substantially blocking the inlet passage and clearing the outlet passage, a single valve performs the tasks of alternatingly closing off and clearing of the inlet passage and the outlet passage. With the reduction of the number of valves, the risk of thrombosis occurring at the valve is accordingly reduced and the complexity and costs of the construction are reduced.

Particularly advantageous embodiments of the invention are set forth in the dependent claims. Catheters and fittings according to such particular embodiments are preferably included in the catheter pump according to the invention.

Further objects, features, effects, advantages and details of the invention are described with reference to examples shown in the drawings.

DETAILED DESCRIPTION

Figure 1:
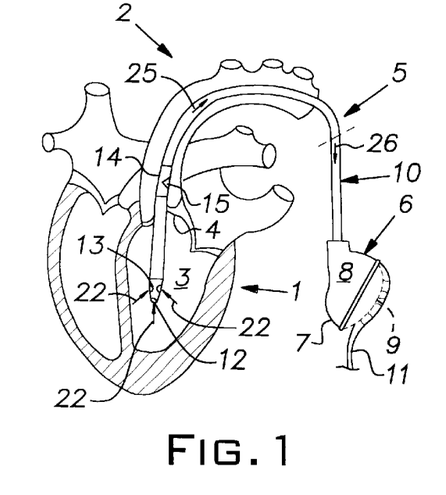
FIGS. 1 and 2 are cut away views of a heart and the aorta into which a catheter pump is inserted.
Figure 2:
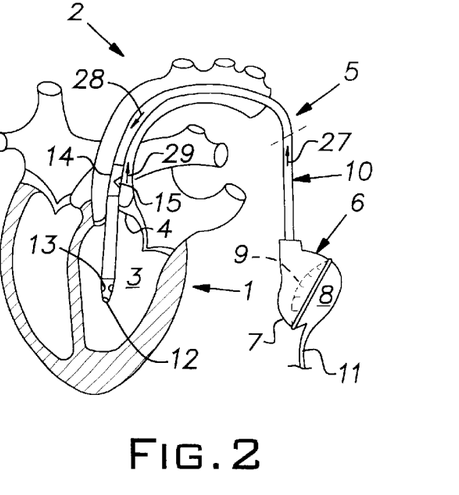

In FIGS. 1 and 2 a heart 1 and a aorta 2 connected thereto are depicted. The heart has a left ventricle 3 and an aortic valve 4.

A pulsatile cardiac assist catheter pump 5 has a displacement device 6 in the form of a rigid housing 7 enclosing a chamber 8 divided by a flexible membrane 9. The catheter pump 5 further has a catheter 10 projecting from that displacement device 6 and communicating with a portion of the chamber 8 on a distal side of the membrane 9 and a pneumatic conduit 11 communicating with a pump drive unit (not shown) and with a portion of the chamber 8 on a proximal side of the membrane 9. The displacement structure 6 can be driven via the pneumatic conduit 11 for alternatingly applying suction for displacing fluid from the catheter 10 to the displacement structure 6 and for applying pressure for displacing fluid from the displacement structure 6 to the catheter 10, thus driving a flow through the catheter 10 which reverses in a pulsating manner. The pump drive unit is preferably controlled to operate in accordance with pulsating contractions and relaxations of the left ventricle 3. To this end, the pump drive unit is connected to a control unit adapted for detecting electrocardiac signals and for controlling the pump in accordance with detected electrocardiac signals.

The catheter 10 projects from the displacement device 6 via an axillary or femoral artery and the aorta 2 into the left ventricle 3.

A distal end portion 12 of the catheter 10 is provided with inlet passages 13. Spaced in proximal direction from the inlet passages 13, the catheter 10 is provided with a fitting 14 having an outlet passage 15 at a distance of 12 cm from the distal tip of the catheter 10. To ensure that in installed condition the outlet is located in a suitable position in the aorta the distance between the distal tip of the catheter and the outlet passage is preferably 8 to 16 cm and more preferably about 10 to 14 cm.

The fitting 14 is shown in more detail in FIGS. 3–6. The catheter pump, the catheter and the fitting as shown in FIGS. 1–6 represent the presently most preferred embodiments of the invention.

The fitting 14 has a tube shaped housing wall 17. In this example, the housing has a circular cross-section, but other cross-sectional shapes are conceivable as well, such as oval, lens-shaped, rectangular, triangular etc. However, smooth outer shapes are preferred in order to interfere as little as possible with the operation of the aortic valve 4.

The fitting 14 further has a coupling 18 for coupling to a distal portion of the catheter 10 on one end and a coupling 19 for coupling to a proximal portion of the catheter 10 on its opposite end. The representation in the drawings of the couplings 18, 19 for coupling to the catheter 10 is of a schematic nature. The couplings are preferably made as is described in applicant's International patent application WO 97/18936.

The fitting 14 has three passages. A first passage 20 through the coupling 18 for coupling to the distal portion of the catheter 10, a second passage 21 through the coupling 19 for coupling to a proximal portion of a catheter 10 and a third passage communicating with the first and second passages 20, 21 which is formed by the opening 15.

Figure 3:
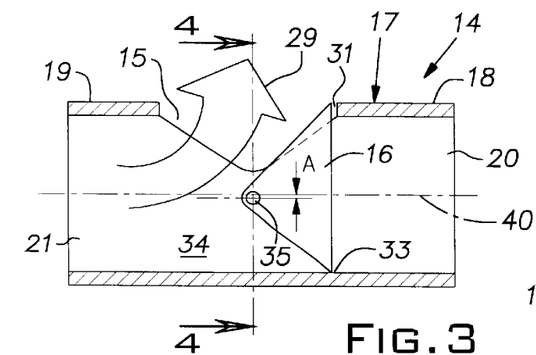
FIG. 3 is a side view in cross-section along the line III—III in FIG. 4 of a fitting according to the invention.
Figure 4:
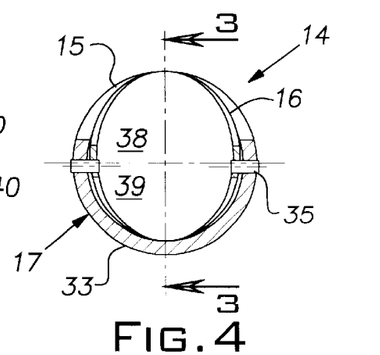
FIG. 4 is a side view in cross-section along the line IV—IV in FIG. 3.

The fitting 14 is further provided with a valve structure for blocking outward blood flow via the inlet passages 13 and inward blood flow via the outlet passage 15. The valve arrangement is formed by a valve body 16 movable between an inlet position substantially obstructing flow through the outlet passage 15—i.e. the third passage of the fitting 14—and allowing flow through the inlet passage 13 and the first passage 20 of the fitting 14 (FIGS. 5 and 6) and an outlet position substantially obstructing flow through the inlet passage 13 and the first passage 20 of the fitting 14 and allowing flow through the outlet passage 15 (FIGS. 3 and 4).

Although it would in principle be possible to control the motions of the valve body 16 actively in accordance with operation of the pump drive unit, it is preferred to control the motions of the valve body 16 passively, such that the valve body 16 is movable from the inlet position (FIGS. 5 and 6) to the outlet position (FIGS. 3 and 4) in response to suction applied by the displacement structure 6 to and via the second passage 21 and movable from the outlet position to the inlet position in response to pressure applied by the displacement structure 6 to and via the second passage 21. Thus, the need of providing a drive unit and provisions for feeding power to the drive unit are avoided, and the costs and complexity of the construction are reduced while the reliability is improved.

Figure 5:
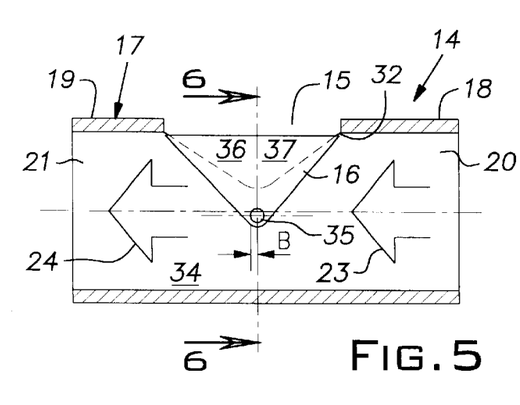
FIG. 5 is a side view in cross-section along the line V—V in FIG. 6 of the fitting according to FIGS. 3 and 4 in a different operating condition.
Figure 6:
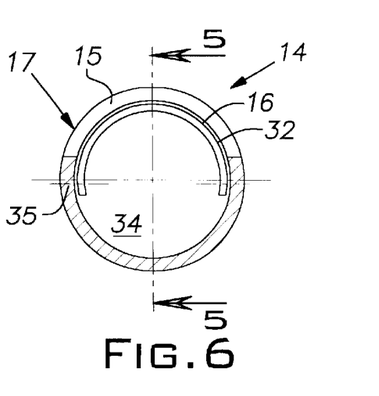
FIG. 6 is a side view in cross-section along the line VI—VI in FIG. 5.

In operation, when the displacement device 6 takes in blood from the catheter 10, the valve body 16 is urged into the position shown in FIGS. 5 and 6 which causes blood to be withdrawn from the left ventricle 3 and through the catheter 10 as is indicated by arrows 22–26 shown in FIGS. 1, 5 and 6, After the desired volume of blood for the support of one stroke has been collected and when it has become time for completing the stroke, the pump drive unit is controlled to reverse from withdrawing air form the chamber 8 to pressing air into the chamber 8. In response, blood is pressed into the catheter 10 and the blood flow in the catheter 10 is reversed as is indicated by the arrows 27, 28 in FIG. 2. In response to the reversal of the blood flow, the valve member 16 is urged from the inlet position shown in FIGS. 5 and 6 into the outlet position shown in FIGS. 3 and 4. This causes the blood flow to be prevented from flowing back through the first passage 20 and the inlet openings 13 (possibly apart from some leakage) and to be forced out of the catheter 10 via the outlet opening 15 in an upstream portion of the aorta 2, as is indicated by arrows 29 in FIGS. 3 and 4.

Since the valve body 16 is located inside the catheter 10, the valve body 16 does not add to the cross-section of the catheter 10, which is advantageous for facilitating insertion of the catheter 10 and to keep damage to tissue of the patient as small as possible. Furthermore, the risk of damaging the valve is reduced as well.

In each operation condition, interspaces 31, 32, 33 between the valve body 16 and the wall 17 of the fitting 14 are each open on at least two opposite sides for allowing blood to flow through the interspaces. This counteracts the formation of stagnation zones where blood is prone to clot. Thus the risk of the formation of thromboses at the valve is further reduced. Thrombogenetic blood flow stagnation zones are further counteracted since the valve body 6 allows some leakage, so that in each operating condition the interspaces are flushed due to the pressure drop over the valve body 16.

In the particular example shown in FIGS. 3–6, the housing wall 17 of the fitting 14 of the catheter 10 bounds a lumen 34 and the outlet opening 15 is formed by an opening in the wall 17.

The valve body 16 is formed by a plate-shaped member which extends closely along and inside a projection of the wall 17 in the area of the opening 15 when in the inlet position shown in FIGS. 5 and 6. When in the outlet position shown in FIGS. 3 and 4, the valve body 16 extends transversely across a section of the lumen 34 on a distal side of the outlet opening 15. The valve body 16 is pivotable between the inlet position and the outlet position about an axis 35 extending across a central portion of the lumen 34 and centrally located behind the opening 15.

When the blood flow through the catheter 10 is directed towards the proximal end, the drag caused by the flow retains the valve body 16 in the position shown in FIGS. 5 and 6. To prevent the valve body 16 from pivoting past the position in front of the opening 15, in this example a distal edge portion-of the valve body 16 is in abutment with a portion of the wall 17 of the fitting 14 bounding a distal side of the opening 15. A particular advantage of this embodiment is, that the pressure in the aorta 2 does not tend to press the valve body 16 away from its position occluding the opening 15, because resulting torques caused by pressure in the aorta 2 higher than pressure in the lumen 34 essentially cancel each other out.

When the flow is reversed, the forces exerted onto valve body 16 by the drag of the blood flow are inverted, which causes the valve body 16 to be entrained to the outlet position shown in FIGS. 3 and 4.

Finally, when the blood flow is reversed again, the valve body 16 is entrained back to the inlet position shown in FIGS. 5 and 6.

In the present example, the lumen 34 has a circular cross-section. Like other round cross-sections, such as oval cross-sections, a circular cross-section provides the advantage of smoothness, which helps to prevent damage to vessels and other tissue of the patient.

The opening 15 is round in a view frontal thereto and wedge-shaped in a side view perpendicular to that frontal view, and the plate-shaped member is curved about axes of curvature transverse to the pivoting axis 35, and round in frontal view and wedge-shaped in a side view perpendicular thereto. This allows a vary large opening in the wall 17 of the fitting 14 to be alternatingly occluded and cleared by a valve body 16 which also clears, respectively occludes the round lumen 34 when in the outlet position extending transversely across the lumen 34.

The opening 15 provided according to the present example is particularly large, because, in side view, opposite sides of the wedge shapes of the opening and of the valve body extend approximately perpendicular to each other, for instance at an angle of 75–105° and preferably about 90° to each other.

In the inlet position, the valve body 16 has a frontal projected area having a portion 36 on a proximal side of the pivoting axis 35 and a portion 37 on a distal side of the axis 35. The portion 36 on the proximal side of the pivoting axis 35 is larger than the portion 37 on the distal side of the pivoting axis 35. This causes a pressure drop over the valve body 16 from the aorta 2 to the lumen 34 to assist retaining the valve body 16 in the inlet position. Conversely, if the pressure drop over the valve body 16 is inverted due to the reversal of the operation of the displacement device 6, this feature supports a quick movement of the valve body 16 out of the inlet position.

As appears particularly clearly from FIG. 4, in the outlet position, the valve body.16 has a frontal projected area having a portion 38 on a side of the pivoting axis 35 where the opening 15 is located and a portion 39 on an opposite side of the pivoting axis 35. The portion 38 on the side of the pivoting axis 35 where the opening 15 is located is larger than the portion 39 on the opposite side of the pivoting axis 35. This difference between the sizes of the frontal area portions 38, 39 on opposite sides of the pivoting axis 35 causes the valve body to be firmly urged into and retained in the outlet position by a pressure drop over the valve body 16 from the proximal side to the distal side as occurs during the outflow of blood under influence of pressure exerted by the displacement device 6. Conversely, if the pressure drop over the valve body 16 is inverted due to the reversal of the operation of the displacement device 6, this feature supports a quick movement of the valve body out of the outlet position.

For the same purpose, the portion of the cross section of the lumen 34 on the side of the pivoting axis 35 where the opening 15 is located is larger than the portion of the cross section of the lumen 34 on the opposite side of that pivoting axis 35.

In the present example, the desired difference in size between the projected frontal area portions 36 and 37 as well as 38 and 39 is obtained by providing that the location of the pivoting axis 35 is on the one hand offset from the central axis 40 of the lumen 34 in a direction away from the opening 15 and on the other hand offset from the center of the opening 15 in a distal direction. These offsets are indicated by reference mark A in FIG. 3 and, respectively, reference mark B in FIG. 4.

Figure 7:
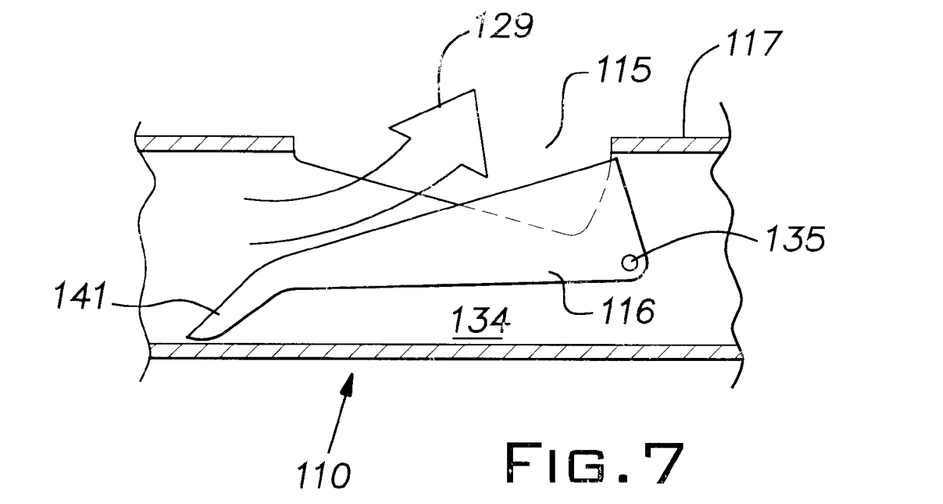
FIG. 7 is a side view in longitudinal cross-section of a section of a catheter according to another embodiment of the invention.
Figure 8:
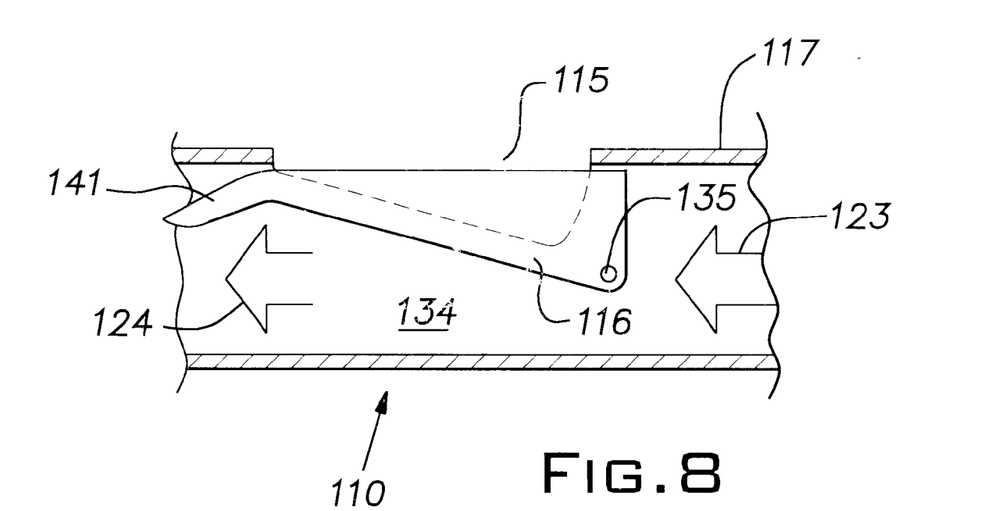
FIG. 8 is a view according to FIG. 7 but in a different operating condition.

In the embodiment shown in FIGS. 7 and 8, an opening 115 is provided in a wall 117 of the catheter 110 in essentially the same position as the opening 15 shown in FIGS. 1 and 2.

The valve body 116 is formed by a plate-shaped member. When in the inlet position, the valve body 116 extends closely along and inside a projection of the wall 117 in the area of the opening 115 (FIG. 8). Furthermore, the valve body 116 has a deflector 141 projecting into the lumen 134 on a proximal side of the valve body 116. When in the outlet position, the valve body 116 extends diagonally across a section of said lumen 134 in the area of the outlet opening 115 (FIG. 7). The valve body 116 is pivotable between the inlet position and the outlet position and is hinged to the wall 117 about an axis 135 closely adjacent a distal end portion of the opening 115.

When the displacement device 6 is operative for drawing blood in proximal direction—as indicated by arrows 123, 124 in FIG. 8—the valve body 116 is urged and retained in its inlet position by the forces exerted by the flow onto the inside of the valve body 116. In order to counteract a pressure drop from the aorta 2 to the interior of the catheter 110, the deflector 141 causes an additional closing force exerted onto the valve body 116. Due to the large distance between the deflector 141 and the pivoting axis 135 where the valve body 116 is hinged to the wall 117, the deflector 141 causes the generation of a substantial closing torque about the axis 135.

When the operation of the displacement device is reversed causing the blood flow to be reversed as well, the blood flow (indicated by arrow 129) hitting the deflector 141 causes the valve body 116 to be opened. The pressure drop over the valve body 116 from the proximal side to the distal side which is subsequently caused causes the valve body 116 to be retained in the outlet position as long as the flow 129 is maintained.

From the above description, it will be apparent to the skilled person, that the present invention can be embodied in many alternative ways other than those described and mentioned above. It is for instance possible to directly mount the valve body in the catheter without the use of a fitting. Other exemplary alternatives are to provide the valve body in the form of a flap connected to the catheter wall or the wall of a fitting by a flexible connection or to provide that the valve body is guided for translatory movement between the inlet position and the outlet position.

What is claimed is:

1. A cardiac assist catheter pump comprising:
   a catheter having a distal end portion, at least one inlet passage in said distal end portion and at least one outlet passage spaced from said distal end portion; and
   a displacement structure;
   said displacement structure communicating with said catheter for alternatingly applying suction for displacing fluid from said catheter to said displacement structure and applying pressure for displacing fluid from said displacement structure to said catheter;
   said catheter comprising a valve arrangement for obstructing outward blood flow via said inlet passage and inward blood flow via said outlet passage; and
   said valve arrangement including a valve body movable between an inlet position obstructing flow through said outlet passage and allowing flow through said inlet passage and an outlet position obstructing flow through said inlet passage and allowing flow through said outlet passage,
   wherein interspaces between said valve body and a wall of the catheter are each at least open on at least two axially opposite sides when the valve body-is in its inlet or outlet position for allowing blood to flow through said interspaces.

2. A catheter pump according to claim 1, wherein said valve body is movable from said inlet position to said outlet position in response to suction applied by said displacement structure and movable from said outlet position to said inlet position in response to pressure applied by said displacement structure.

3. A catheter pump according to claim 1, wherein said outlet passage is spaced 8–16 cm from a distal tip of said distal end portion of said catheter.

4. A cardiac assist catheter having:
   a distal end portion;
   a connection for coupling the catheter to a displacement structure for alternatingly applying suction for displacing fluid from the catheter to said displacement structure and for applying pressure for displacing fluid from said displacement structure to the catheter;
   at least one inlet passage in said distal end portion;
   at least one outlet passage spaced from said distal end portion; and
   a valve arrangement for obstructing outward blood flow via said inlet passage and inward blood flow via said outlet passage;
   wherein said valve arrangement includes a valve body movable between an inlet position obstructing flow through said outlet passage and allowing flow through said inlet passage and an outlet position obstructing flow through said inlet passage and allowing flow through said outlet passage,
   wherein interspaces between said valve body and a wall of the catheter are each at least open on at least two axially opposite sides when the valve body is in its inlet or outlet position for allowing blood to flow through said interspaces.

5. A catheter according to claim 4, wherein said valve body is movable from said inlet position to said outlet position in response to suction applied via said connection and movable from said outlet position to said inlet position in response to pressure applied via said connection.

6. A catheter according to claim 4, wherein said valve body is located inside the catheter.

7. A catheter according to claim 4, wherein said outlet passage is spaced 8–16 cm from a distal tip of said distal end portion of said catheter.

8. A cardiac assist catheter having:
   a distal end portion;
   a connection for coupling the catheter to a displacement structure for alternatingly applying suction for displacing fluid from the catheter to said displacement structure and for applying pressure for displacing fluid from said displacement structure to the catheter;
   at least one inlet passage in said distal end portion;
   at least one outlet passage spaced from said distal end portions; and
   a valve arrangement for obstructing outward blood flow via said inlet passage and inward blood flow via said outlet passage;
   wherein said valve arrangement includes a valve body movable between an inlet position obstructing flow through said outlet passage and allowing flow through said inlet passage and an outlet position obstructing flow through said inlet passage and allowing flow through said outlet passage,
   said catheter further comprising a wall bounding a lumen, wherein said outlet passage is formed by an opening in said wall;
   said valve body:
      is a plate-shaped member,
      when in said inlet position, extends closely along and inside a projection of said wall in the area of said outlet opening,
      when in said outlet position extends transversely across a section of said lumen on a distal side of said outlet opening, and
      is pivotable between said inlet position and said outlet position about an axis extending across a central portion of said lumen and centrally located behind said outlet opening.

9. A catheter according to claim 8, wherein
   said lumen has a round cross section;
   said outlet opening is round in a view frontal thereto and wedge-shaped in a side view perpendicular to said frontal view; and
   said plate-shaped member is curved about an axis of curvature transverse to said pivoting axis, round in frontal view and wedge-shaped in a side view perpendicular thereto.

10. A catheter according to claim 9, wherein, in side view, opposite sides of said wedge shapes of said outlet opening and of said valve body extend at an angle of 75–105° to each other.

11. A catheter according to claim 9, wherein, in said inlet position, said valve body has a frontal projected area having a first portion on a proximal side of said pivoting axis and a second portion on a distal side of said pivoting axis, said first portion being larger than said second portion.

12. A catheter according to claim 8, wherein, in said outlet position, said valve body has a frontal projected area having a first portion on a side of said pivoting axis where said outlet opening is located and a second portion on an opposite side of said pivoting axis, said first portion being larger than said second portion.

13. A catheter according to claim 12, wherein said pivoting axis extends across said lumen, and wherein said lumen has a cross-sectional area having a portion on a side of said pivoting axis where said outlet opening is located and a portion on an opposite side of said axis, said portion on said side of said pivoting axis where said opening is located being larger than said portion on said opposite side of said pivoting axis.

14. A cardiac assist catheter having:
   a distal end portion;
   a connection for coupling the catheter to a displacement structure for alternatingly applying suction for displacing fluid from the catheter to said displacement structure and for applying pressure for displacing fluid from said displacement structure to the catheter;
   at least one inlet passage in said distal end portion;
   at least one outlet passage spaced from said distal end portion; and
   a valve arrangement for obstructing outward blood flow via said inlet passage and inward blood flow via said outlet passage;
   wherein said valve arrangement includes a valve body movable between an inlet position obstructing flow through said outlet passage and allowing flow through said inlet passage and an outlet position obstructing flow through said inlet passage and allowing flow through said outlet passage,
   said catheter further comprising a wall bounding a lumen, wherein said outlet passage is formed by an opening in said wall;

said valve body:
is a plate-shaped member,
when in said inlet position extends closely along and inside a projection of said wall in the area of said outlet opening,
has a deflector projecting into said lumen from a proximal side of said valve body,
when in said outlet position, extends diagonally across a section of said lumen in the area of said outlet opening,
is pivotable between said inlet position and said outlet position, and
is hinged to said wall in an area closely adjacent a distal end portion of said outlet opening.

15. A fitting for a cardiac assist catheter comprising:
a tube shaped housing having a coupling for coupling to a distal portion of a catheter on one end and a coupling for coupling to a proximal portion of a catheter on an opposite end;
a first passage through said coupling for coupling to a distal portion of a catheter;
a second passage through said coupling for coupling to a proximal portion of a catheter;
a third passage communicating with said first and second passages; and
a valve body movable between an inlet position obstructing flow through said third passage and allowing flow through said first passage and an outlet position obstructing flow through said first passage and allowing flow through said third passage,
wherein interspaces between said valve body and a wall of the fitting are each at least open on at least two axially opposite sides when the valve body is in its inlet or outlet position for allowing blood to flow through said interspaces.

16. A fitting according to claim 15, wherein said valve body is movable from said inlet position to said outlet position in response to suction applied to said second passage and movable from said outlet position to said inlet position in response to pressure applied to said second passage.

17. A fitting according to claim 16, wherein said valve body is located inside the fitting.

18. A fitting for a cardiac assist catheter comprising:
a tube shaped housing having a coupling for coupling to a distal portion of a catheter on one end and a coupling for coupling to a proximal portion of a catheter on an opposite end;
a first passage through said coupling for coupling to a distal portion of a catheter;
a second passage through said coupling for coupling to a proximal portion of a catheter;
a third passage communicating with said first and second passages; and
a valve body movable between an inlet position obstructing flow through said third passage and allowing flow through said first passage and an outlet position obstructing flow through said first passage and allowing flow through said third passage,
said fitting further comprising a wall bounding a lumen, wherein said outlet passage is formed by an opening in said wall;
said valve body:
is a plate-shaped member,
when in said inlet position, extends closely along and inside a projection of said wall in the area of said outlet opening, p2 when in said outlet position, extends transversely across a section of said lumen between said outlet opening and said first passage, and
is pivotable between said inlet position and said outlet position about a pivoting axis extending across a central portion of said lumen and centrally located behind said outlet opening.

19. A fitting according to claim 18, wherein
said lumen has a round cross section,
said outlet opening is round in a view frontal thereto and wedge-shaped in a side view perpendicular to said frontal view, and
said plate-shaped member is curved about an axis of curvature transverse to said pivoting axis, round in frontal view and wedge-shaped in a side view perpendicular thereto.

20. A fitting according to claim 19, wherein, in side view, opposite sides of said wedge shapes of said outlet opening and of said valve body extend at an angle of 75–105° to each other.

21. A fitting according to claim 19, wherein, in said inlet position, said valve body has a frontal projected area having a first portion on a first side of said pivoting axis where said second passage is located and a second portion on a second side of said pivoting axis where said first passage is located, said first portion being larger than said second portion.

22. A fitting according to claim 18, wherein, in said outlet position, said valve body has a frontal projected area having a first portion on a side of said pivoting axis where said outlet opening is located and a second portion on an opposite side of said pivoting axis, said first portion being larger than said second portion.

23. A fitting according to claim 22, wherein said pivoting axis extends across said lumen, and wherein said lumen has a cross-sectional area having a portion on a side of said pivoting axis where said outlet opening is located and a portion on an opposite side of said pivoting axis, said portion on said side of said pivoting axis where said outlet opening is located being larger than said portion on said opposite side of said pivoting axis.

24. A fitting for a cardiac assist catheter comprising:
a tube shaped housing having a coupling for coupling to a distal portion of a catheter on one end and a coupling for coupling to a proximal portion of a catheter on an opposite end;
a first passage through said coupling for coupling to a distal portion of a catheter;
a second passage through said coupling for coupling to a proximal portion of a catheter;
a third passage communicating with said first and second passages; and
a valve body movable between an inlet position obstructing flow through said third passage and allowing flow through said first passage and an outlet position obstructing flow through said first passage and allowing flow through said third passage, said fitting further comprising a wall bounding a lumen, wherein said outlet passage is formed by an opening in said wall;

said valve body:
- is a plate-shaped member,
- when in said inlet position, extends closely along and inside a projection of said wall in the area of said opening,
- has a deflector projecting into said lumen from a side of said valve body closely to said second passage,
- when in said outlet position, extends diagonally across a section of said lumen in the area of said outlet opening,
- is pivotable between said inlet position and said outlet position, and
- is hinged to said wall in an area closely adjacent an end portion of said outlet opening on the side of said first passage.

* * * * *

UNITED STATES PATENT AND TRADEMARK OFFICE
CERTIFICATE OF CORRECTION

PATENT NO. : 6,398,714 B1
DATED : June 4, 2002
INVENTOR(S) : Verkerke et al.

It is certified that error appears in the above-identified patent and that said Letters Patent is hereby corrected as shown below:

<u>Title page,</u>
Item [56], References Cited, FOREIGN PATENT DOCUMENTS, please delete document 6 and insert therefore
-- WO           WO 98/57698         12/1998 --.

<u>Column 4,</u>
Line 45, please delete "portion of" and insert therefore -- portion of --.

<u>Column 5,</u>
Line 28, please delete "body.16" and insert therefore -- body 16 --.

<u>Column 6,</u>
Line 62, please delete "body-is" and insert therefore -- body is --.

Signed and Sealed this

Eighth Day of October, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.    : 6,398,714 B1
DATED         : June 4, 2002
INVENTOR(S)   : G.J. Verkerke, A. van der Plaats and G. Rakhorst

It is certified that error appears in the above-identified patent and that said Letters Patent is hereby corrected as shown below:

<u>Column 10,</u>
Line 5, please delete -- p2 --.

Signed and Sealed this

Fourth Day of March, 2003

*Attest:*

*Attesting Officer*

JAMES E. ROGAN
*Director of the United States Patent and Trademark Office*